(12) United States Patent
Ertas et al.

(10) Patent No.: US 7,498,950 B1
(45) Date of Patent: Mar. 3, 2009

(54) APPARATUS AND METHOD FOR USING RFID TO TRACK USE OF A COMPONENT WITHIN A DEVICE

(75) Inventors: Hasan Ertas, Sunnyvale, CA (US); Brannon P. Wells, San Jose, CA (US); Rajeshwari Srinivasan, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 490 days.

(21) Appl. No.: 11/216,241

(22) Filed: Aug. 30, 2005

Related U.S. Application Data

(62) Division of application No. 10/662,012, filed on Sep. 11, 2003, now Pat. No. 7,154,378.

(51) Int. Cl.
*G08B 21/00* (2006.01)
*G08B 13/14* (2006.01)
*A62B 1/04* (2006.01)

(52) U.S. Cl. ............... 340/679; 340/572.1; 340/539.12; 600/101; 600/103; 600/104; 600/300; 600/118; 348/65; 348/73; 700/65; 250/336.1; 250/200; 356/300

(58) Field of Classification Search .................. 340/679
See application file for complete search history.

(56) References Cited

U.S. PATENT DOCUMENTS

| | | | |
|---|---|---|---|
| 5,821,854 A | 10/1998 | Dorinski et al. | |
| 6,490,490 B1 | 12/2002 | Uchikubo et al. | |
| 6,697,764 B2 | 2/2004 | Corby, Jr. et al. | |
| 7,154,378 B1 * | 12/2006 | Ertas et al. | 340/5.85 |
| 2003/0060682 A1 | 3/2003 | Handa et al. | |
| 2003/0097042 A1 | 5/2003 | Elno | |
| 2003/0100294 A1 | 5/2003 | Hosono | |
| 2003/0174205 A1 | 9/2003 | Amling et al. | |
| 2003/0182584 A1 | 9/2003 | Banes et al. | |
| 2003/0204724 A1 | 10/2003 | Ayyagari et al. | |

OTHER PUBLICATIONS

U.S. Appl. No. 11/342,474, Applicant: Hasan Ertas, et al., filed Jan. 30, 2006 entitled Endoscopy Device With Integrated RFID and External Network Capability.

* cited by examiner

*Primary Examiner*—Donnie L Crosland
(74) *Attorney, Agent, or Firm*—Flynn, Thiel, Boutell & Tanis, P.C.

(57) ABSTRACT

RFID circuitry is used in an endoscopic light source unit to track cumulative light bulb use information. An inductively powered RFID tag is affixed to the light bulb assembly, and communicates wirelessly with an RF transceiver within the light source unit via a low-frequency modulation wave. The RFID tag includes memory which stores a value representing cumulative duration of use of the light bulb. The transceiver reads the value from the RFID tag and communicates the value to control circuitry in the light source unit, which tracks use of the light bulb within the light source unit. Based on such tracking, the transceiver periodically updates the value in the RFID tag via the wireless link. Cumulative bulb usage hours is displayed on the light source unit. The RFID tag also may store a custom password and/or other information.

17 Claims, 6 Drawing Sheets

APPARATUS AND METHOD FOR USING RFID TO TRACK USE OF A COMPONENT WITHIN A DEVICE

This is a divisional of U.S. patent application Ser. No. 10/662,012, filed on Sep. 11, 2003, now U.S. Pat. No. 7,154,378 by H. Ertas et al., which is incorporated herein by reference.

FIELD OF THE INVENTION

At least one embodiment of the present invention pertains to tracking use of a component within a device, and more particularly, to tracking the cumulative duration of use of a replaceable light source in a light source unit for an endoscopic imaging system.

BACKGROUND

Endoscopy in the medical field allows internal features of the body of a patient to be viewed without the use of traditional, fully-invasive surgery. FIGS. 1A and 1B collectively illustrate an endoscopic imaging system such as commonly used in the medical field. FIG. 1A generally illustrates the image generation and display components of the system, while FIG. 1B illustrates the data acquisition components of the system. FIG. 1B shows the data acquisition components, which include an endoscope 2, a camera 3, and a coupler 6 connecting the endoscope 2 to the camera 3. The camera 3 acquires color video image data of internal features of a body through a system of lenses in the endoscope 2. FIG. 1A shows the image generation and display components of the system, which include a camera control unit (CCU) 4, a light source unit 7, a monitor 9, a video recorder 10, and a printer 11, which are stored on a mobile cart 12. Various other system configurations are also possible.

High-intensity light is provided to the endoscope 2 by the light source unit 7 through a flexible light conduit 8, such as fiber optic cable. Operation of the camera system can be controlled from the CCU 4. The camera 3 is coupled to the camera control unit (CCU) 4 by a flexible transmission line 5. The transmission line 5 conveys power to the camera 3, video image data from the camera 3 to the CCU 4, and various control signals bi-directionally between the camera 3 and the CCU 4. Image data received by the CCU 4 from the camera 3 are processed and converted to video images by the CCU 4, which are displayed on the monitor 9, and if desired, recorded by the video recorder 10 and/or used to generate static images that can be printed by printer 11.

Light from the light source unit 7 is generated by a replaceable light bulb (not shown in FIG. 1) inside the light source unit 7. The light bulb has a limited lifetime, i.e., eventually it will fail. It is extremely undesirable for the light bulb to fail during surgery, due to the potential danger to the patient posed by a sudden loss of illumination or a delay in surgery to replace the bulb, the risk of explosion of the bulb, and other potential adverse consequences. Therefore, it is necessary to replace the light bulb before a failure occurs.

After a number of hours of use, which can be predicted with reasonable accuracy, the likelihood of failure of the light bulb increases substantially. This number of hours may be considered to be the light bulb's maximum useful lifetime. The manufacturer of the light bulb or the light source unit typically specifies the useful lifetime and/or a warranty period of the light bulb, in terms of hours of use. The manufacturer may offer an incentive to the user (customer) to replace the light bulb prior to expiration of the warranty period and/or the useful lifetime.

However, it is burdensome for users to keep track of the number of hours the light bulb has been used. The light bulb cannot inherently track the number of hours that it has been used, as it lacks any circuitry to do so. Physical limitations that hinder access to low voltage levels on the light bulb generally prevent the use of any conductively powered circuitry to perform this task.

At least one known design for a light source unit attempts to address this problem. The light source unit keeps track of bulb use on its own, without actually knowing the true cumulative use of the bulb, and provides a bulb hours display on the front panel of the light source unit. In this design, the user has to reset the bulb hours display whenever the bulb is replaced. Also, if the user replaces the bulb with a used bulb, the light source unit has no way of knowing this, and there is no way to cause the light source unit to accurately display the true hours of use of the replacement bulb.

BRIEF DESCRIPTION OF THE DRAWINGS

One or more embodiments of the present invention are illustrated by way of example and not limitation in the figures of the accompanying drawings, in which like references indicate similar elements and in which.

DETAILED DESCRIPTION

Figure 1:
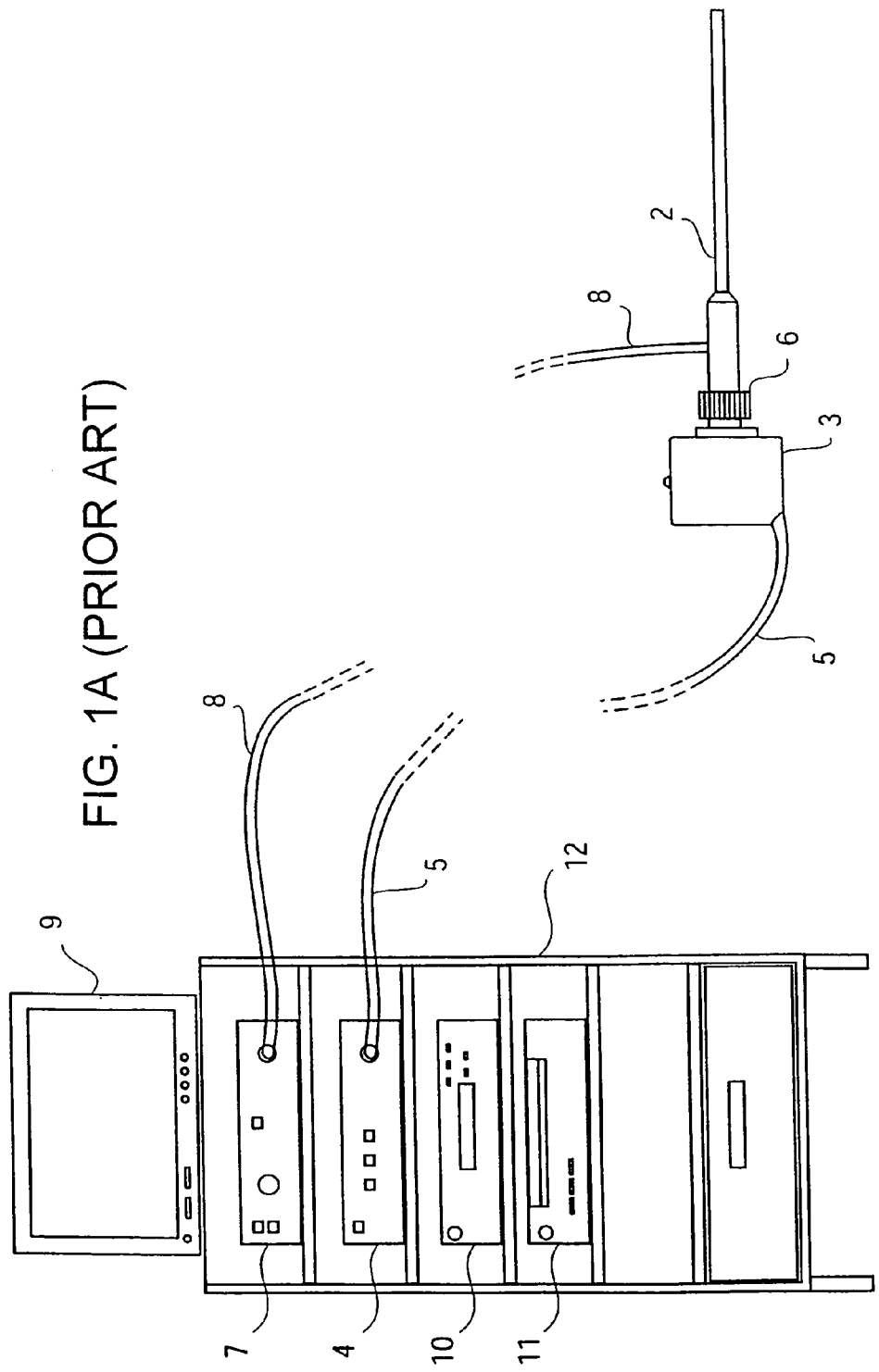
FIGS. 1A and 1B illustrate a conventional endoscopic imaging system.

A method and apparatus for tracking the cumulative duration of use of a replaceable light source in a light source unit for an endoscopic imaging system are described. Note that in this description, references to "one embodiment" or "an embodiment" mean that the feature being referred to is included in at least one embodiment of the present invention. Further, separate references to "one embodiment" or "an embodiment" in this description do not necessarily refer to the same embodiment; however, such embodiments are also not mutually exclusive unless so stated, and except as will be readily apparent to those skilled in the art from the description. For example, a feature, structure, act, etc. described in one embodiment may also be included in other embodiments. Thus, the present invention can include a variety of combinations and/or integrations of the embodiments described herein.

In accordance with the invention, radio frequency identification (RFID) circuitry is used in a light source unit for use in endoscopic surgery, to store and communicate cumulative light source use information. An inductively powered wireless RFID tag is affixed to an assembly containing the light bulb or other type of light source in the light source unit. To facilitate description, it is henceforth assumed herein that the light source is a light bulb. However, in other embodiments, a different type of light source may be used, such as one or more light-emitting diodes (LEDs), for example.

The RFID tag on the light bulb assembly communicates with a conductively-powered radio frequency (RF) transceiver in the light source unit via a low-frequency modulation wave through the air (i.e., wirelessly). The RFID tag includes non-volatile memory (e.g., flash or some form of EPROM) which stores a value representing the cumulative duration of use of the light bulb.

The value is initially set by the manufacturer of the light bulb assembly. When the light bulb assembly is installed in the light source unit and the light source unit is powered on, the transceiver reads the value from the RFID tag and communicates the value to control circuitry in the light source unit. The control circuitry tracks use of the light bulb within the light source unit, and based on such tracking, periodically causes the transceiver to update the stored value in the RFID tag via the wireless link. Cumulative bulb usage hours is displayed on the front panel of the light source unit based on the current value stored in the RFID tag.

The RFID tag is powered by the same modulation wave that is used for communication between the transceiver and the RFID tag. Wireless communication between the transceiver and the RFID tag is achieved using an LC resonance circuit driven by the transceiver, which inductively couples with a corresponding LC resonance circuit within the RFID tag.

This approach enables accurate tracking of cumulative light bulb use, independently of the light source unit in which the bulb is used. The user never needs to reset the bulb usage display when the bulb is replaced. Hence, users are enabled to order and install replacement bulbs before they exceed the warranty period or fail unexpectedly. Furthermore, this approach enables the bulb usage display to remain accurate even if the light bulb is replaced by a used bulb.

This design also requires no direct contact between the RFID tag and either the antenna or the transceiver. The RFID tag also (or alternatively) may store various other types of data, such as a custom password that protects the system from external interruptions or intrusions, as well as other information.

Note that the approach introduced herein is not limited in application to use with a light bulb or any other component of a light source unit. The approach introduced herein can be used to provide accurate tracking of cumulative use or other information associated with potentially any component in any piece of equipment. To facilitate explanation of the invention, however, the description which follows is directed to tracking use of a light bulb (or other light source) in a light source unit for use in endoscopy.

Figure 2:
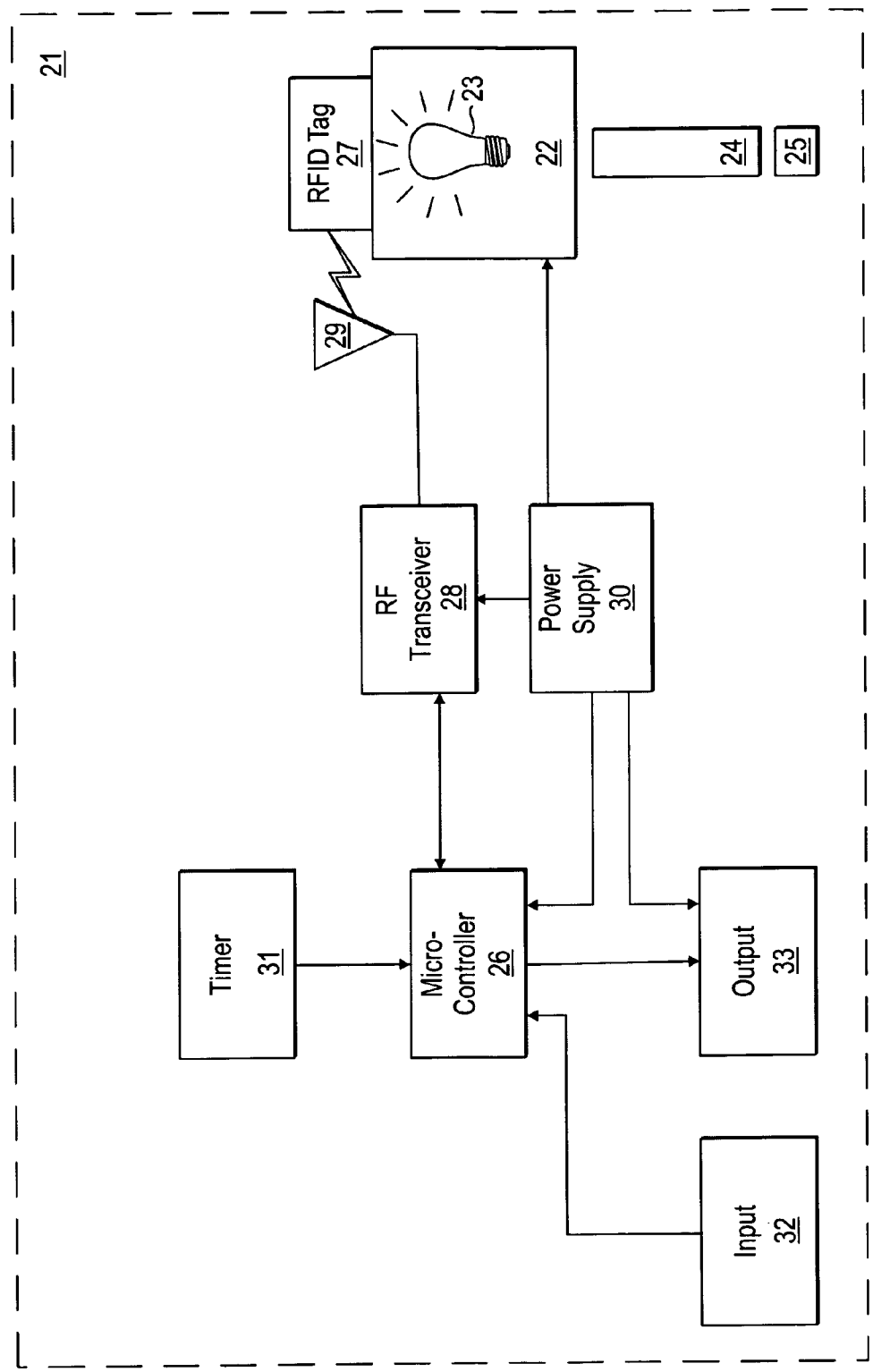
FIG. 2 is a block diagram of a light source unit for use in an endoscopic camera system.

FIG. 2 is a block diagram showing the components of a light source unit 21 for use in an endoscopic imaging system. Light source unit 21 may be used in the same manner as light source unit 7 in FIG. 1. The light source unit 21 includes a light bulb assembly 22, which includes a light bulb 23 to generate high-intensity light to be transmitted through an endoscope. In other embodiments, the light bulb 23 may be replaced by another form of light source, such as one or more light-emitting diodes (LEDs), for example. The light source unit 21 further includes an internal light coupler 24 optically coupled to the light bulb 23 and to an external light conduit connector 25 on the front plate of the light source unit 21. During operation, light from the light bulb 23 is transmitted through the internal light coupler 24 and the light conduit connector 25 to a flexible light conduit such as fiber-optic cable (not shown in FIG. 2) connected externally to the light source unit 21, the opposite end of which is optically coupled to the endoscope.

The light source unit 21 further includes a microcontroller 26, an RFID tag 27, an RF transceiver 28, an antenna 29, a power supply 30, a timer 31, one or more input devices 32, and one or more output devices 33. The light source unit 21 may also contain components that are not shown or described, which are not germane to the present invention.

The microcontroller controls and coordinates the overall operation of the light source unit 21. The microcontroller may include its own internal memory (not shown) and may be programmable.

The input devices 32 may include, for example, one or more switches, buttons, or other devices, to control various functions of the light source unit 21, such as power on/off, mode selection, light intensity, etc. The output devices 33 are used to provide the user with information to facilitate operation of the light source unit 21, including cumulative usage hours of the light bulb 23, as well as feedback on parameters such as light intensity, etc. The output devices 33 may include one or more display devices, such as a liquid crystal display (LCD), cathode ray tube (CRT), or the like, and/or one or more sound output devices (e.g., audio speakers). Furthermore, although the input devices 32 and output devices 33 are shown as being separate, an input device 32 and an output device 33 may be combined in a single device, such as a touchscreen display.

All of the active components shown in FIG. 2 except the RFID tag 27 are conductively powered by the power supply 30. The RFID tag 27 is powered by RF induction from the antenna 29.

Figure 3:
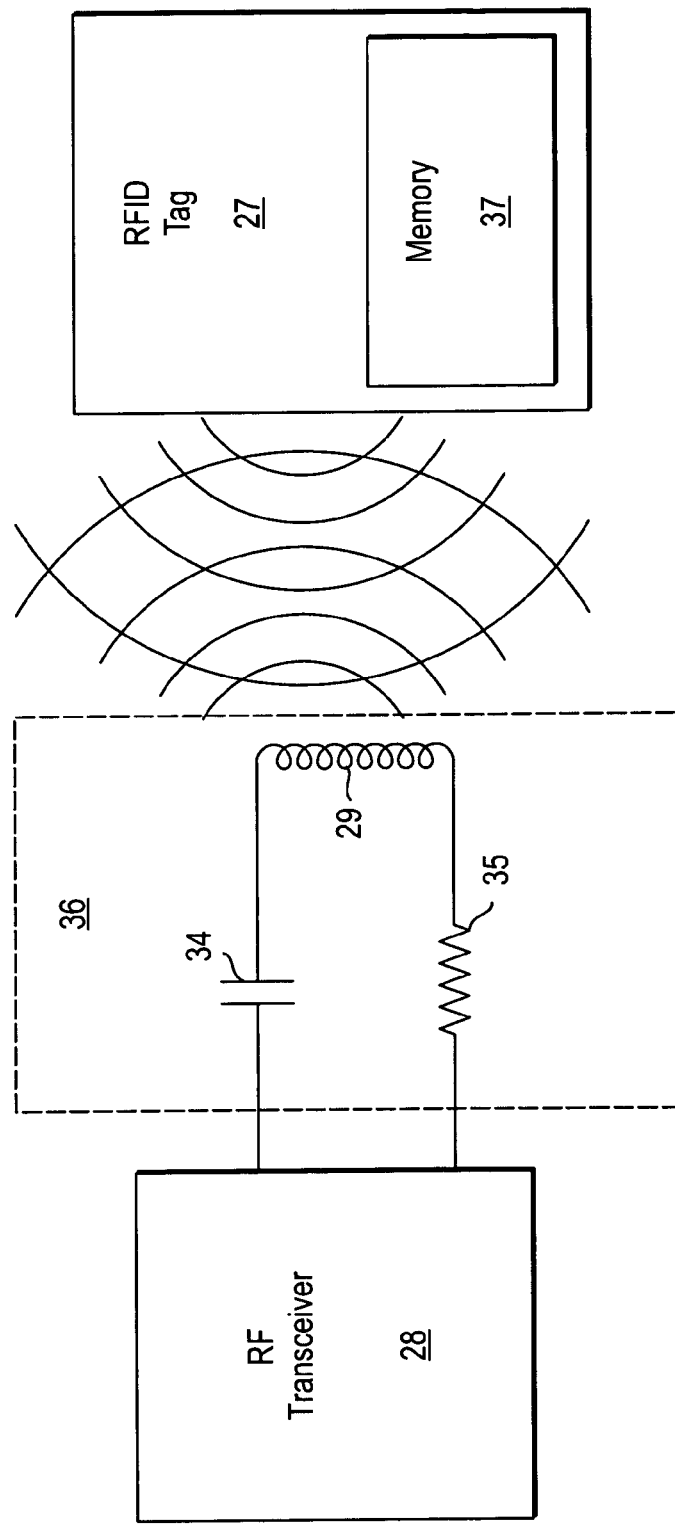
FIG. 3 shows a portion of a light source unit that relates to communication with an RFID tag.

In certain embodiments, the antenna 29 is a simple coil (i.e., an inductor) that forms part of a series LC resonance circuit, which is shown in FIG. 3. As can be seen from FIG. 3, the LC resonance circuit 36 is driven by the RF transceiver 28. The LC resonance circuit 36 includes the antenna (coil) 29, a capacitor 34, and a resistor 35, all coupled in series with the signal output of the RF transceiver 28. The antenna 29 inductively couples with a corresponding LC resonance circuit (not shown) within the RFID tag 27. The purpose of the resonance circuit 36 is to increase the size of the sinusoidal wave across the antenna 29, as discussed further below.

The resulting large-scale voltage wave produced at the antenna 29 charges a small capacitor that is attached to the resonance circuit in the RFID tag 27, provided the RFID tag 27 is positioned close to the antenna 29 (e.g., within about one inch, for the embodiments described herein). The small capacitor in the RFID tag 27 is used to drive the circuitry within the RFID tag 27 for a short period of time, i.e., as long as the charge remains on the small capacitor. Once the capacitor in the RFID tag 27 is charged and the RFID tag 27 is operating, the large-scale voltage wave is pulse-amplitude modulated to provide communication between the RF transceiver 28 and the RFID tag 27.

The LC resonance circuit 36 is designed so that its natural resonant frequency is substantially equal to the frequency of the sinusoidal wave produced by the RF transceiver 28, subject to minor tuning. In general, the natural resonant frequency, $f_r$, of a series LC circuit is defined as $f_r = 1/(2\pi\sqrt{(LC)})$. Thus, in the embodiment discussed above, L in the foregoing formula is the inductance value of the antenna 29, and C is the capacitance value of the capacitor 34. In practice, this frequency varies due to factors such as the mutual inductance created by the coupling of the secondary coil in the RFID tag (not shown), and the variation in the values of the antenna 29 and capacitor 34. Therefore, for optimum results, the inductance and capacitance values of the antenna 29 and capacitor 34, respectively, should be tuned by measuring secondary power across the load at different frequencies around the calculated natural resonant frequency for the specific application load.

In one embodiment, the RF transceiver 28 is the HTRC11001T reader chip from Philips Semiconductors ("Philips"), and the RFID tag 27 is the HT2DC20S20M tag from Philips. In this embodiment, the RF transceiver 28 transmits a 50-100 V peak-to-peak sinusoidal wave at a frequency of about 125 kHz; the capacitor 34 has a capacitance value of about 3.6 nanofarads; the antenna 29 has an inductance value of about 447 microhenries; and the resistor 35 has a resistance value of about 22 ohms. The antenna 29 is mounted within the light source unit 21 so that its center is about one inch from the center of the RFID tag 27.

Figure 4:
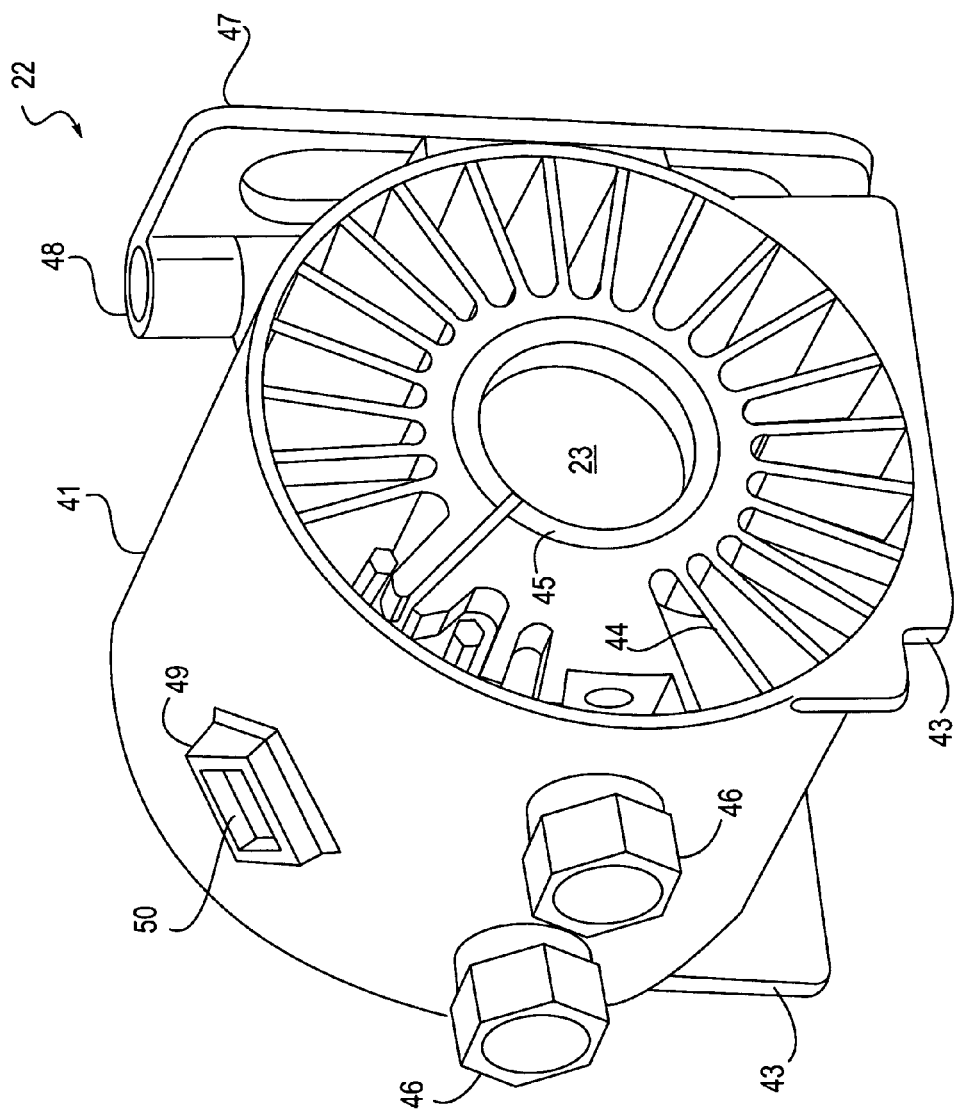
FIG. 4 is a perspective view of a light bulb assembly with an RFID tag affixed thereto.
Figure 5:
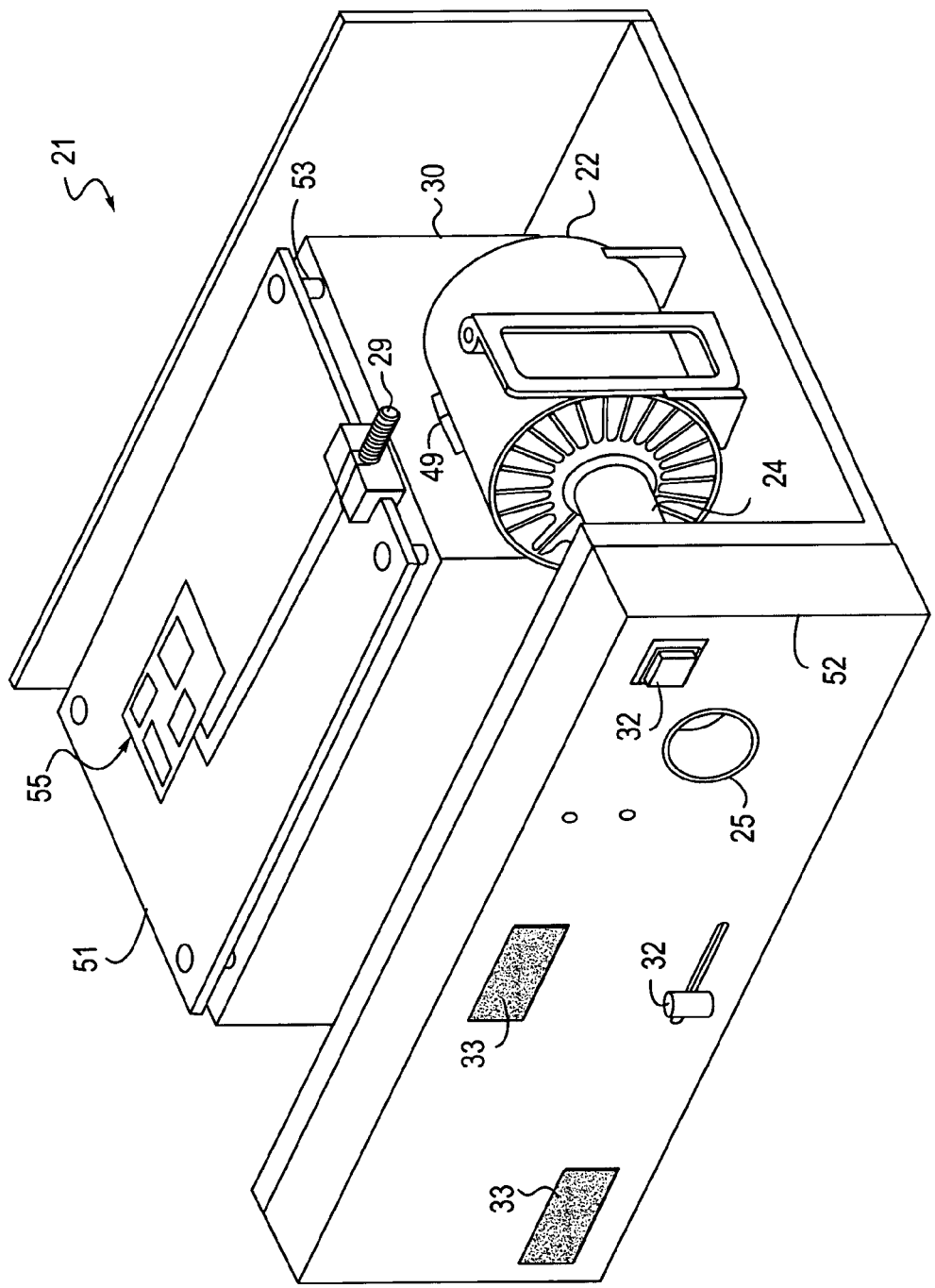
FIG. 5 is a perspective installation drawing of a light source unit for use in an endoscopic imaging system, including a light bulb assembly with an RFID tag affixed thereto.

FIG. 4 shows an embodiment of the light bulb assembly 22, illustrating how the RFID tag 27 can be affixed to it. The light bulb assembly 22 can be installed in the light source unit 21 has as shown in FIG. 5. The light bulb assembly 22 includes a hollow cylindrical housing 41, a heat sink installed within the interior of the housing 41, and the light bulb 23, which is the light source of the light source unit 21. The housing 41 is made of plastic and includes two flat extensions 43 from the front and back of the lower portion of its exterior surface, which provide a stable base for the light bulb assembly 22. The heat sink comprises a hollow metal cylindrical hub 45 and a number of flat metal vanes 44 that extend radially from the hub 45 almost to the interior surface of the housing 41. The light bulb 23 is installed in the interior of the hub 45.

When the light bulb assembly 22 is installed in the light source unit 21, electrical terminals (not shown) of the light bulb 23 electrically connect to the power supply 30 via two socket connectors 46 on the light bulb assembly 22, which mate with two corresponding conductive prongs (terminals) on the power supply 30. The light bulb assembly 22 is removable from the light source unit 21 (e.g., for inspection or replacement) and includes a handle to facilitate removal. The handle 47 is mounted on a hinge 48 attached to the exterior of the housing 41. The light bulb assembly 22 is removed from the light source unit 21 by pulling on the handle 47, causing the light source assembly 22 to slide away from the power supply 30 so as to disconnect it from the power supply 30.

To accommodate the RFID tag 27, the light bulb assembly 22 also includes small rectangular pedestal 49 on the upper portion of the exterior surface of the housing 41. The pedestal may be formed integrally with the exterior surface of the housing 41, or it may be manufactured as a separate component and then affixed to the exterior surface of the housing 41. As shown in FIG. 4, the pedestal 49 is located slightly offset from the top of the housing 41 (at about the "10 o'clock" position when viewing the light bulb end on), in order to provide the RFID tag 27 with an optimum position and orientation relative to the antenna 29, as shown in FIG. 5. In other embodiments, different positions and orientations of the antenna 29 and pedestal 49 may be used.

The RFID tag 27 is typically embodied as a conventionally packaged microelectronic chip. During manufacture of the light bulb assembly 22, the RFID tag is placed within a shallow depression 50 at the top of the pedestal 49. The RFID tag 27 is then fixed in this position by applying a layer of glue (e.g., epoxy) over it, which completely encases the RFID tag 27 and fixes it to the housing 41 when the glue is hardened/cured. Once hardened/cured, the glue serves both to fix the RFID tag 27 to the housing 41 and to protect the RFID tag 27 from damage and tampering.

FIG. 5 shows how the light bulb assembly 22 can be installed in the light source unit 21, to allow wireless communication between the RF transceiver 28 and the RFID tag 27. More specifically, FIG. 5 shows a perspective view of the light source unit 21, with its cover removed so as to expose certain significant internal components, including the light bulb assembly 22, the power supply 30, and a circuit board 51. The light source unit 21 has a front panel 52 that provides a user interface, including the input controls 32, the output devices 33, and the light conduit connector 25. One of the output devices 33 (an LCD, for example) is used to display light bulb usage hours. Other conventional and well-known components of the light source unit 21 which are not germane to the present invention are not shown in FIG. 5.

Figure 6:
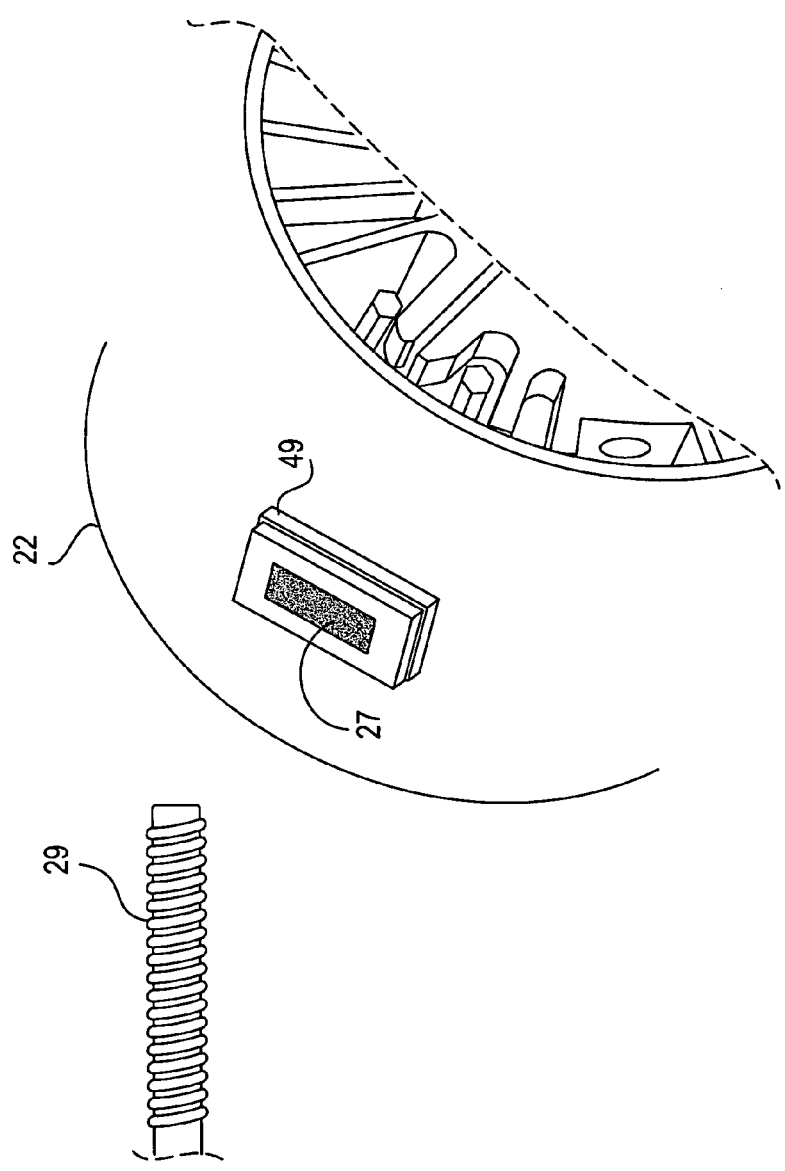
FIG. 6 is close-up view showing the relative position and orientation of the antenna and the RFID tag.

The light bulb assembly 22 is electrically connected to the power supply 30 and is installed adjacent to the power supply 30, such that the light bulb 23 is optically aligned with the optical coupler 24. The circuit board 51 is mounted on top of the power supply 30 and is raised above the top surface of the power supply 30 by spacers 53 to facilitate heat dissipation. Mounted on the circuit board 51 are the antenna 29 and a set of microelectronic devices 55, which includes the RF transceiver 28, the microcontroller 26, and the timer 31 (see FIG. 2). The antenna 29 extends horizontally beyond the edge of the circuit board 51 in a position such that the center of the antenna 29 is about one inch from the center of the RFID tag 27 mounted on the light bulb assembly 22, when the light bulb assembly 22 is installed in the light source unit 21. FIG. 6 is close-up view showing the relative position and orientation of the antenna 29 and the RFID tag 27.

When the light bulb assembly 22 is manufactured, an initial value representing bulb usage hours is stored in the memory 37 (see FIG. 3) within the RFID tag 27. Since the manufacturer of the light bulb assembly 22 is not necessarily the manufacturer of the whole light source unit 21, this process of storing the initial value may be done using transceiver circuitry that is similar to that shown in FIG. 2 but not necessarily part of a light source unit 21. The initial value will normally be zero or a small non-zero value to reflect the manufacturer's testing of the light bulb 23.

When the fully assembled light source unit 21 is powered on, the microcontroller 26 causes the RF transceiver to read the value of bulb usage hours stored in the RFID tag 27. The RF transceiver 28 passes the value to the microcontroller 26, which causes one of the output devices 33 (e.g., an LCD) to display to the user an indication of the cumulative duration of use of the light bulb. The microcontroller 26 keeps track of further bulb use based on timing input from the timer 31. Periodically (e.g., once per minute), the microcontroller 26 causes the RF transceiver 28 to update (rewrite) the value stored in the RFID tag 27 to reflect further use of the light bulb, and the output indication to the user is updated accordingly.

Besides bulb usage hours, other types of information may also be stored in the memory 37 within the RFID tag 27, such as a password or other authentication data, which can be used to protect the light source unit from external interruptions for intrusions. Thus, the password may be used to selectively enable or disable use of the light source unit. As another example, the RFID tag 27 may store data identifying the light bulb 23 or the light bulb assembly 22 (e.g., by manufacturer, model number and serial number). As yet another example, the microcontroller 26 may be configured to cause the RF transceiver 28 to store in the RFID tag 27 data identifying the light source unit 21 (e.g., by manufacturer, model number and serial number). This data could then be used, for example, by the manufacturer to determine whether the light bulb assembly 22 has been used improperly in a light source unit for which it is not qualified or compatible, if the light bulb assembly 22 (or the entire light source unit 21) requires service after a failure. The memory 37 in the RFID tag 27 can also be used to store performance data relating to any one or more components in the light source unit 21 (which may include diagnostic data relating to operation or failure of the component), which is not limited to the light bulb 23 or the light bulb assembly 22. This data can be used by the manufacturer to provide better service and to improve future product designs. Thus, essentially any kind of data can be stored in the RFID tag 27. In general, after the initial data is set in the RFID tag 27 by the manufacturer, the microcontroller 26 determines what data is stored in and read from the RFID tag 27 and when such data is stored or read, according to its programming.

Thus, a method and apparatus for tracking the cumulative duration of use of a replaceable light source in a light source unit for an endoscopic camera system have been described. Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A light source unit for use in an endoscopic imaging system, the light source unit comprising:
   a light source;
   a light source housing containing the light source;
   an RFID tag attached to the light source housing, the RFID tag including stored data;
   an RF transceiver;
   an antenna coupled to the RF transceiver and mounted so as to permit wireless communication between the RFID tag and the transceiver; and
   a controller to control the RF transceiver to read the data stored in the RFID tag using said wireless communication, and to selectively enable or disable use of the light source unit based on the data stored in the RFID tag.

2. A light source unit as recited in claim 1, wherein the controller is further to control the RF transceiver to read the performance data from the RFID tag using said wireless communication, the light source unit further comprising an output device for outputting an indication of the performance data read from the RFID tag to an entity external to the light source unit.

3. A light source unit for use in an endoscopic imaging system, the light source unit comprising:
   a light source which is removable from the light source unit and which is usable in each of a plurality of light source units;
   a light source housing containing the light source;
   an RFID tag attached to the light source housing, the RFID tag including stored data, including data identifying each light source unit in which the light source has been used;
   an RF transceiver;
   an antenna coupled to the RF transceiver and mounted so as to permit wireless communication between the RFID tag and the transceiver; and
   a controller to control the RF transceiver to update the data stored in the RFID tag to include data which identifies the light source unit.

4. A light source unit as recited in claim 3, wherein the controller is further to control the RF transceiver to read the data stored in the RFID tag using said wireless communication, the light source unit further comprising an output device for outputting an indication of the data stored in the RFID tag to an entity external to the light source unit.

5. A light source unit for use in an endoscopic imaging system, the light source unit comprising:
   a light source;
   a light source housing containing the light source;
   an RFID tag attached to the light source housing;
   an RF transceiver;
   an antenna coupled to the RF transceiver and mounted so as to permit wireless communication between the RFID tag and the transceiver; and
   a controller to control the RF transceiver to store performance data in the RFID tag using said wireless communication, the performance data relating to performance of a component in the light source unit other than the light source.

6. A light source unit as recited in claim 5, wherein the controller is further to control the RF transceiver to read the performance data from the RFID tag using said wireless communication, the light source unit further comprising means for outputting an indication of the performance data read from the RFID tag to an entity external to the light source unit.

7. A method of operating a device designed for use in an endoscopic medical procedure, the method comprising:
   using a wireless link within the device to read data stored in a memory attached to a removable component within the device;
   manually providing input data to the device; and
   comparing the data read from the memory with the input data to selectively enable or disable use of the component within the device.

8. A method as recited in claim 7, wherein the device comprises a light source unit.

9. A method as recited in claim 8, wherein the component comprises a light source within the light source unit.

10. A method of operating a device designed for use in an endoscopic medical procedure, the method comprising:
    installing a replaceable component within the device;
    in response to the replaceable component being installed within the device, using a wireless link within the device to store data identifying the device in a memory attached to the replaceable component; and
    operating the device to control the replaceable component disposed within the device.

11. A method as recited in claim 10, wherein the device comprises a light source unit.

12. A method as recited in claim 11, wherein the component comprises a light source within the light source unit.

13. A method as recited in claim 10, wherein the replaceable component is usable as a component in each of a plurality of similar devices, and wherein the memory comprises an RFID tag, and including the step of storing identifying data for each of the plurality of similar devices in which the replaceable component has been used.

14. A method of operating a device designed for use in an endoscopic medical procedure, the method comprising:
    operating a replaceable component within the device;
    obtaining performance data relating to a component of the device other than said replaceable component; and
    using a wireless link within the device, storing the performance data in a memory attached to the replaceable component.

15. A method as recited in claim 14, wherein the device comprises a light source unit.

16. A method as recited in claim 15, wherein the replaceable component comprises a light source within the light source unit.

17. A method as recited in claim 15, wherein the replaceable component comprises a light source housing containing a light source therein.

* * * * *